(12) United States Patent
Dunn et al.

(10) Patent No.: US 12,682,798 B1
(45) Date of Patent: Jul. 14, 2026

(54) SYSTEMS AND METHODS FOR AUTOMATED, ARTIFICIAL INTELLIGENCE BASED MONITORING OF, AND/OR ALERTING FOR, DIGITAL OUT OF HOME DISPLAY UNITS

(71) Applicant: Manufacturing Resources International, Inc., Alpharetta, GA (US)

(72) Inventors: William Dunn, Alpharetta, GA (US); Mike Brown, Cumming, GA (US)

(73) Assignee: Manufacturing Resources International, Inc., Alpharetta, GA (US)

( * ) Notice: Subject to any disclaimer, the term of this patent is extended or adjusted under 35 U.S.C. 154(b) by 0 days.

(21) Appl. No.: 19/338,524

(22) Filed: Sep. 24, 2025

(51) Int. Cl.
*G09G 3/00* (2006.01)
*G01N 33/00* (2006.01)
(Continued)

(52) U.S. Cl.
CPC ......... *G09G 3/006* (2013.01); *G01N 33/0063* (2013.01); *G06N 3/08* (2013.01);
(Continued)

(58) Field of Classification Search
CPC ............... G09G 3/006; G09G 2330/12; G01N 33/0063; G06N 3/08; G01R 31/2805;
(Continued)

(56) References Cited

U.S. PATENT DOCUMENTS 3,504,528 A    4/1970  Weinberg et al.
3,807,220 A    4/1974  Ottenstein et al.
             (Continued)

FOREIGN PATENT DOCUMENTS

CN    203277867 U    11/2013
CN    110441008 A    11/2019
             (Continued)

OTHER PUBLICATIONS

Photo Research, Inc., PR®-650 SpectraScan® Colorimeter, 1999, 2 pages.
(Continued)

*Primary Examiner* — Raul J Rios Russo
(74) *Attorney, Agent, or Firm* — Standley Law Group LLP; Jeffrey S. Standley; Adam J. Smith

(57) ABSTRACT

Systems and methods for automated, artificial intelligence ("AI") based monitoring of, and alerting for, digital out of home display units are disclosed. The display units are installed at various geographic locations and each include a display subassembly connected to a structural subassembly, sensors for measuring conditions, airflow pathways with fans, and electronics for operation and control. A monitoring subsystem receives data from the display units, including sensor and operational status data, tags the data with a unique identifier, and analyzes the data using an AI model to identify if the data indicates that any of the display units are experiencing abnormal conditions or maintenance needs. The AI model is trained on historical data including sensor and operational status data from same or different display units tagged as normal or abnormal. The monitoring subsystem generates an alert and electronic service request for the abnormal conditions and maintenance needs.

20 Claims, 6 Drawing Sheets

(51) Int. Cl.

| | | |
|---|---|---|
| *G01R 31/28* | (2006.01) | |
| *G01R 31/52* | (2020.01) | |
| *G06N 3/08* | (2023.01) | |

(52) U.S. Cl.

CPC ...... *G01R 31/2805* (2013.01); *G01R 31/2829* (2013.01); *G01R 31/2853* (2013.01); *G01R 31/2884* (2013.01); *G01R 31/52* (2020.01); *G09G 2330/12* (2013.01)

(58) Field of Classification Search

CPC   G01R 31/52; G01R 31/2884; G01R 31/2853; G01R 31/2829; G01R 31/002

USPC .......................................................... 324/537

See application file for complete search history.

(56) References Cited

U.S. PATENT DOCUMENTS

| | | | |
|---|---|---|---|
| 4,527,804 | A | 7/1985 | Spencer |
| 5,162,785 | A | 11/1992 | Fagard |
| 5,168,961 | A | 12/1992 | Schneider |
| 5,228,339 | A | 7/1993 | Maresca, Jr. et al. |
| 5,322,051 | A | 6/1994 | Patterson et al. |
| 5,351,201 | A | 9/1994 | Harshbarger, Jr. et al. |
| 5,590,831 | A | 1/1997 | Manson et al. |
| 5,751,346 | A | 5/1998 | Dozier et al. |
| 5,786,801 | A | 7/1998 | Ichise |
| 5,952,992 | A | 9/1999 | Helms |
| 6,042,443 | A | 3/2000 | Carella et al. |
| 6,144,359 | A | 11/2000 | Grave |
| 6,157,143 | A | 12/2000 | Bigio et al. |
| 6,158,692 | A | 12/2000 | Abild et al. |
| 6,215,411 | B1 | 4/2001 | Gothard |
| 6,222,841 | B1 | 4/2001 | Taniguchi |
| 6,259,492 | B1 | 7/2001 | Imoto et al. |
| 6,374,187 | B1 | 4/2002 | Knight et al. |
| 6,384,736 | B1 | 5/2002 | Gothard |
| 6,421,694 | B1 | 7/2002 | Nawaz et al. |
| 6,509,911 | B1 | 1/2003 | Shimotono |
| 6,526,807 | B1 | 3/2003 | Doumit et al. |
| 6,546,294 | B1 | 4/2003 | Kelsey et al. |
| 6,553,336 | B1 | 4/2003 | Johnson et al. |
| 6,556,258 | B1 | 4/2003 | Yoshida et al. |
| 6,587,525 | B2 | 7/2003 | Jeong et al. |
| 6,701,143 | B1 | 3/2004 | Dukach et al. |
| 6,753,842 | B1 | 6/2004 | Williams et al. |
| 6,771,795 | B1 | 8/2004 | Isnardi |
| 6,812,851 | B1 | 11/2004 | Dukach et al. |
| 6,821,179 | B2 | 11/2004 | Ando |
| 6,850,209 | B2 | 2/2005 | Mankins et al. |
| 6,955,170 | B1 | 10/2005 | Mullins et al. |
| 6,968,375 | B1 | 11/2005 | Brown |
| 7,007,545 | B1 | 3/2006 | Martinek |
| 7,064,672 | B2 | 6/2006 | Gothard |
| 7,319,862 | B1 | 1/2008 | Lincoln et al. |
| 7,330,002 | B2 | 2/2008 | Joung |
| 7,380,265 | B2 | 5/2008 | Jensen et al. |
| 7,391,317 | B2 | 6/2008 | Abraham et al. |
| 7,451,332 | B2 | 11/2008 | Culbert et al. |
| 7,474,294 | B2 | 1/2009 | Leo et al. |
| 7,516,223 | B2 | 4/2009 | Whitehead |
| 7,577,458 | B2 | 8/2009 | Lin |
| 7,581,094 | B1 | 8/2009 | Apostolopoulos et al. |
| 7,595,785 | B2 | 9/2009 | Jang |
| 7,612,278 | B2 | 11/2009 | Sitrick et al. |
| 7,636,927 | B2 | 12/2009 | Zigmond et al. |
| 7,658,787 | B2 | 2/2010 | Morse et al. |
| 7,675,862 | B2 | 3/2010 | Pham et al. |
| 7,679,279 | B2 | 3/2010 | Kamio et al. |
| 7,751,813 | B2 | 7/2010 | Varanda |
| 7,764,280 | B2 | 7/2010 | Shiina |
| 7,774,633 | B1 | 8/2010 | Harrenstien et al. |
| 7,795,821 | B2 | 9/2010 | Jun |
| 7,882,728 | B2 | 2/2011 | Kizaki et al. |
| 7,889,852 | B2 | 2/2011 | Whitehead |
| 7,949,893 | B1 | 5/2011 | Knaus et al. |
| 8,074,627 | B2 | 12/2011 | Siddiqui et al. |
| 8,212,921 | B2 | 7/2012 | Yun |
| 8,218,812 | B2 | 7/2012 | Sugimoto et al. |
| 8,248,203 | B2 | 8/2012 | Hanwright et al. |
| 8,336,369 | B2 | 12/2012 | Mahoney |
| 8,441,574 | B2 | 5/2013 | Dunn et al. |
| 8,483,554 | B2 | 7/2013 | Takimoto et al. |
| 8,601,252 | B2 | 12/2013 | Mendelow et al. |
| 8,612,608 | B2 | 12/2013 | Whitehead |
| 8,654,302 | B2 | 2/2014 | Dunn et al. |
| 8,689,343 | B2 | 4/2014 | De Laet |
| 8,767,165 | B2 | 7/2014 | Dunn |
| 8,854,595 | B2 | 10/2014 | Dunn |
| 8,881,576 | B2 | 11/2014 | Schwartz et al. |
| 9,026,686 | B2 | 5/2015 | Dunn et al. |
| 9,147,194 | B1 | 9/2015 | Le et al. |
| 9,363,262 | B1 | 6/2016 | Wilkes |
| 9,760,151 | B1 | 9/2017 | Hou |
| 10,170,076 | B2 | 1/2019 | Wang et al. |
| 10,174,519 | B1 | 1/2019 | Carpenter et al. |
| 10,311,763 | B2 | 6/2019 | Greenfield |
| 10,578,658 | B2 | 3/2020 | Dunn et al. |
| 10,593,175 | B1 | 3/2020 | Jennings et al. |
| 11,131,453 | B2 | 9/2021 | Kim et al. |
| 11,402,940 | B2 | 8/2022 | Dunn |
| 11,645,029 | B2 | 5/2023 | Newnham et al. |
| 11,803,344 | B2 | 10/2023 | Newnham et al. |
| 11,965,804 | B2 | 4/2024 | Dunn et al. |
| 11,972,672 | B1 | 4/2024 | Dunn |
| 12,393,241 | B1 | 8/2025 | Dunn et al. |
| 2002/0019933 | A1 | 2/2002 | Friedman et al. |
| 2002/0026354 | A1 | 2/2002 | Shoji et al. |
| 2002/0065046 | A1 | 5/2002 | Mankins et al. |
| 2002/0112026 | A1 | 8/2002 | Fridman et al. |
| 2002/0120721 | A1 | 8/2002 | Eilers et al. |
| 2002/0147648 | A1 | 10/2002 | Fadden et al. |
| 2002/0152425 | A1 | 10/2002 | Chaiken et al. |
| 2002/0163513 | A1 | 11/2002 | Tsuji |
| 2002/0163916 | A1 | 11/2002 | Oskouy et al. |
| 2002/0164962 | A1 | 11/2002 | Mankins et al. |
| 2002/0190972 | A1 | 12/2002 | Ven de Van |
| 2002/0194365 | A1 | 12/2002 | Jammes |
| 2002/0194609 | A1 | 12/2002 | Tran |
| 2003/0031128 | A1 | 2/2003 | Kim et al. |
| 2003/0039312 | A1 | 2/2003 | Horowitz et al. |
| 2003/0061316 | A1 | 3/2003 | Blair et al. |
| 2003/0097497 | A1 | 5/2003 | Esakov |
| 2003/0098881 | A1 | 5/2003 | Nolte et al. |
| 2003/0115591 | A1 | 6/2003 | Weissmueller, Jr. et al. |
| 2003/0117714 | A1 | 6/2003 | Nakamura et al. |
| 2003/0132514 | A1 | 7/2003 | Liebeskind |
| 2003/0161354 | A1 | 8/2003 | Bader et al. |
| 2003/0177269 | A1 | 9/2003 | Robinson et al. |
| 2003/0192060 | A1 | 10/2003 | Levy |
| 2003/0196208 | A1 | 10/2003 | Jacobson |
| 2003/0214242 | A1 | 11/2003 | Berg-johansen |
| 2003/0230991 | A1 | 12/2003 | Muthu et al. |
| 2004/0036697 | A1 | 2/2004 | Kim et al. |
| 2004/0138840 | A1 | 7/2004 | Wolfe |
| 2004/0158872 | A1 | 8/2004 | Kobayashi |
| 2004/0194131 | A1 | 9/2004 | Ellis et al. |
| 2004/0210419 | A1 | 10/2004 | Wiebe et al. |
| 2004/0243940 | A1 | 12/2004 | Lee et al. |
| 2004/0252400 | A1 | 12/2004 | Blank et al. |
| 2004/0253947 | A1 | 12/2004 | Phillips et al. |
| 2004/0255848 | A1 | 12/2004 | Yudasaka |
| 2005/0033840 | A1 | 2/2005 | Nisani et al. |
| 2005/0070335 | A1 | 3/2005 | Jitsuishi et al. |
| 2005/0071252 | A1 | 3/2005 | Henning et al. |
| 2005/0073518 | A1 | 4/2005 | Bontempi |
| 2005/0088984 | A1 | 4/2005 | Chin et al. |
| 2005/0123001 | A1 | 6/2005 | Craven et al. |
| 2005/0132036 | A1 | 6/2005 | Jang et al. |
| 2005/0179554 | A1 | 8/2005 | Lu |
| 2005/0216939 | A1 | 9/2005 | Corbin |
| 2005/0231457 | A1 | 10/2005 | Yamamoto et al. |
| 2005/0258921 | A1 | 11/2005 | Puskar et al. |
| 2005/0267943 | A1 | 12/2005 | Castaldi et al. |

(56)     References Cited

U.S. PATENT DOCUMENTS

| | | |
|---|---|---|
| 2005/0289061 A1 | 12/2005 | Kulakowski et al. |
| 2005/0289588 A1 | 12/2005 | Kinnear |
| 2006/0007107 A1 | 1/2006 | Ferguson |
| 2006/0022616 A1 | 2/2006 | Furukawa et al. |
| 2006/0150222 A1 | 7/2006 | McCafferty et al. |
| 2006/0160614 A1 | 7/2006 | Walker et al. |
| 2006/0269216 A1 | 11/2006 | Wiemeyer et al. |
| 2007/0039028 A1 | 2/2007 | Bar |
| 2007/0154060 A1 | 7/2007 | Sun |
| 2007/0157260 A1 | 7/2007 | Walker |
| 2007/0168539 A1 | 7/2007 | Day |
| 2007/0200513 A1 | 8/2007 | Ha et al. |
| 2007/0214812 A1 | 9/2007 | Wagner et al. |
| 2007/0237636 A1 | 10/2007 | Hsu |
| 2007/0268241 A1 | 11/2007 | Nitta et al. |
| 2007/0273519 A1 | 11/2007 | Ichikawa et al. |
| 2007/0274400 A1 | 11/2007 | Murai et al. |
| 2007/0286107 A1 | 12/2007 | Singh et al. |
| 2007/0291198 A1 | 12/2007 | Shen |
| 2008/0008471 A1 | 1/2008 | Dress |
| 2008/0019147 A1 | 1/2008 | Erchak et al. |
| 2008/0024268 A1 | 1/2008 | Wong et al. |
| 2008/0034205 A1 | 2/2008 | Alain et al. |
| 2008/0037466 A1 | 2/2008 | Ngo et al. |
| 2008/0037783 A1 | 2/2008 | Kim et al. |
| 2008/0055297 A1 | 3/2008 | Park |
| 2008/0104631 A1 | 5/2008 | Krock et al. |
| 2008/0111958 A1 | 5/2008 | Kleverman et al. |
| 2008/0112601 A1 | 5/2008 | Warp |
| 2008/0136770 A1 | 6/2008 | Peker et al. |
| 2008/0163291 A1 | 7/2008 | Fishman et al. |
| 2008/0185976 A1 | 8/2008 | Dickey et al. |
| 2008/0218501 A1 | 9/2008 | Diamond |
| 2008/0246871 A1 | 10/2008 | Kupper et al. |
| 2008/0266554 A1 | 10/2008 | Sekine et al. |
| 2008/0267328 A1 | 10/2008 | Ianni et al. |
| 2008/0278099 A1 | 11/2008 | Bergfors et al. |
| 2008/0281165 A1 | 11/2008 | Rai et al. |
| 2008/0303918 A1 | 12/2008 | Keithley |
| 2008/0313691 A1 | 12/2008 | Cholas et al. |
| 2009/0009997 A1 | 1/2009 | Sanfilippo et al. |
| 2009/0015400 A1 | 1/2009 | Breed |
| 2009/0034283 A1 | 2/2009 | Albright et al. |
| 2009/0036190 A1 | 2/2009 | Brosnan et al. |
| 2009/0079416 A1 | 3/2009 | Vinden et al. |
| 2009/0104989 A1 | 4/2009 | Williams et al. |
| 2009/0129556 A1 | 5/2009 | Ahn |
| 2009/0152445 A1 | 6/2009 | Gardner, Jr. |
| 2009/0164615 A1 | 6/2009 | Akkanen |
| 2009/0273568 A1 | 11/2009 | Milner |
| 2009/0315867 A1 | 12/2009 | Sakamoto et al. |
| 2010/0017526 A1 | 1/2010 | Jagannath et al. |
| 2010/0037274 A1 | 2/2010 | Meuninck et al. |
| 2010/0060550 A1 | 3/2010 | McGinn et al. |
| 2010/0083305 A1 | 4/2010 | Acharya et al. |
| 2010/0149567 A1 | 6/2010 | Kanazawa et al. |
| 2010/0177157 A1 | 7/2010 | Stephens et al. |
| 2010/0177158 A1 | 7/2010 | Walter |
| 2010/0177750 A1 | 7/2010 | Essinger et al. |
| 2010/0198983 A1 | 8/2010 | Monroe et al. |
| 2010/0226091 A1 | 9/2010 | Dunn |
| 2010/0231563 A1 | 9/2010 | Dunn et al. |
| 2010/0237697 A1 | 9/2010 | Dunn et al. |
| 2010/0299556 A1 | 11/2010 | Taylor et al. |
| 2011/0019636 A1 | 1/2011 | Fukuoka et al. |
| 2011/0047567 A1 | 2/2011 | Zigmond et al. |
| 2011/0058326 A1 | 3/2011 | Idems et al. |
| 2011/0078536 A1 | 3/2011 | Han et al. |
| 2011/0173853 A1 | 7/2011 | Leveque |
| 2011/0283199 A1 | 11/2011 | Schuch et al. |
| 2012/0105424 A1 | 5/2012 | Lee et al. |
| 2012/0203872 A1 | 8/2012 | Luby et al. |
| 2012/0302343 A1 | 11/2012 | Hurst et al. |
| 2012/0308191 A1 | 12/2012 | Chung et al. |
| 2013/0007110 A1 | 1/2013 | Centner |

| | | | |
|---|---|---|---|
| 2013/0162908 A1 | 6/2013 | Son et al. | |
| 2013/0173358 A1 | 7/2013 | Pinkus | |
| 2013/0269531 A1* | 10/2013 | Crabtree | B01D 46/0005 |
| | | | 55/497 |
| 2013/0282154 A1 | 10/2013 | Chappell et al. | |
| 2014/0002747 A1 | 1/2014 | Macholz | |
| 2014/0009893 A1 | 1/2014 | Lai | |
| 2014/0074344 A1* | 3/2014 | Amirpour | G07C 5/008 |
| | | | 701/29.6 |
| 2014/0172174 A1 | 6/2014 | Poss et al. | |
| 2014/0230526 A1 | 8/2014 | Willemin et al. | |
| 2014/0287671 A1 | 9/2014 | Slessman | |
| 2015/0136851 A1* | 5/2015 | Harding | G06K 7/0095 |
| | | | 235/438 |
| 2015/0169827 A1 | 6/2015 | LaBorde | |
| 2015/0193074 A1 | 7/2015 | Cudak et al. | |
| 2015/0250021 A1 | 9/2015 | Stice et al. | |
| 2015/0316944 A1 | 11/2015 | Thellend | |
| 2016/0034240 A1 | 2/2016 | Kreiner et al. | |
| 2016/0112521 A1 | 4/2016 | Lawson et al. | |
| 2016/0125468 A1 | 5/2016 | Staneluis et al. | |
| 2016/0125772 A1 | 5/2016 | Li et al. | |
| 2016/0256021 A1 | 9/2016 | Jolin et al. | |
| 2016/0292744 A1 | 10/2016 | Strimaitis et al. | |
| 2016/0358530 A1 | 12/2016 | Schuch et al. | |
| 2017/0075777 A1 | 3/2017 | Dunn et al. | |
| 2017/0082433 A1 | 3/2017 | Huo et al. | |
| 2017/0083043 A1 | 3/2017 | Bowers et al. | |
| 2017/0091822 A1 | 3/2017 | Tian et al. | |
| 2017/0138814 A1 | 5/2017 | Dempsey et al. | |
| 2017/0163519 A1 | 6/2017 | Bowers et al. | |
| 2017/0219457 A1 | 8/2017 | Keil et al. | |
| 2017/0242502 A1 | 8/2017 | Gray et al. | |
| 2017/0242534 A1 | 8/2017 | Gray | |
| 2017/0256051 A1 | 9/2017 | Dwivedi et al. | |
| 2017/0315886 A1 | 11/2017 | Helmick et al. | |
| 2018/0027635 A1 | 1/2018 | Roquemore, III | |
| 2018/0080670 A1 | 3/2018 | Carlyon et al. | |
| 2018/0089717 A1 | 3/2018 | Morin et al. | |
| 2018/0128708 A1 | 5/2018 | Cirino | |
| 2018/0181091 A1 | 6/2018 | Funk et al. | |
| 2018/0268783 A1 | 9/2018 | Woo | |
| 2018/0284758 A1 | 10/2018 | Cella et al. | |
| 2018/0306052 A1 | 10/2018 | Lammers et al. | |
| 2018/0314103 A1 | 11/2018 | Dunn et al. | |
| 2018/0356470 A1* | 12/2018 | Hindle | G01R 1/025 |
| 2019/0087042 A1 | 3/2019 | Van Ostrand et al. | |
| 2019/0096202 A1 | 3/2019 | Seelman | |
| 2019/0096300 A1* | 3/2019 | Lin | G09G 3/3275 |
| 2019/0122082 A1 | 4/2019 | Cuban et al. | |
| 2019/0171331 A1 | 6/2019 | Gray et al. | |
| 2019/0317049 A1* | 10/2019 | Ferdous | G01N 27/72 |
| 2019/0367148 A1 | 12/2019 | Kehlenbeck et al. | |
| 2020/0012383 A1 | 1/2020 | Wang et al. | |
| 2020/0019363 A1 | 1/2020 | Newnham et al. | |
| 2020/0272269 A1 | 8/2020 | Dunn | |
| 2021/0174715 A1 | 6/2021 | Holloway et al. | |
| 2021/0397292 A1 | 12/2021 | Dunn | |
| 2022/0132681 A1 | 4/2022 | Dunn et al. | |
| 2022/0147168 A1 | 5/2022 | Lee et al. | |
| 2022/0260872 A1 | 8/2022 | Dunn et al. | |
| 2023/0029615 A1 | 2/2023 | Dunn et al. | |
| 2023/0032626 A1 | 2/2023 | Brown | |
| 2023/0048815 A1 | 2/2023 | Newnham et al. | |
| 2023/0052966 A1 | 2/2023 | Newnham et al. | |
| 2023/0056061 A1 | 2/2023 | Dunn et al. | |
| 2023/0160774 A1 | 5/2023 | Dunn et al. | |
| 2023/0164964 A1 | 5/2023 | Dunn et al. | |
| 2023/0333423 A1 | 10/2023 | Dunn et al. | |
| 2023/0384277 A1 | 11/2023 | Dunn et al. | |
| 2024/0032238 A1 | 1/2024 | Dunn et al. | |
| 2024/0144806 A1 | 5/2024 | Dunn | |
| 2024/0201040 A1 | 6/2024 | Dunn et al. | |
| 2025/0149005 A1 | 5/2025 | Dunn et al. | |
| 2025/0227902 A1 | 7/2025 | O'Connor | |

(56)          References Cited

U.S. PATENT DOCUMENTS

FOREIGN PATENT DOCUMENTS

| CN | 114503233 | A | 5/2022 |
| CN | 217384567 | U | 9/2022 |
| EP | 0313331 | B1 | 2/1994 |
| EP | 1628087 | A1 | 2/2006 |
| EP | 1821538 | A1 | 8/2007 |
| EP | 2351369 | A2 | 8/2011 |
| JP | 61-234690 | A | 10/1986 |
| JP | 61-251901 | A | 11/1986 |
| JP | 7-74224 | A | 3/1995 |
| JP | 2000122575 | A | 4/2000 |
| JP | 3080628 | B2 | 8/2000 |
| JP | 2002064842 | A | 2/2002 |
| JP | 2002209230 | A | 7/2002 |
| JP | 2005-211449 | A | 8/2005 |
| JP | 2005-211451 | A | 8/2005 |
| JP | 2005236469 | A | 9/2005 |
| JP | 2005333568 | A | 12/2005 |
| JP | 2010282109 | A | 12/2010 |
| KR | 200361111 | Y1 | 9/2004 |
| KR | 10-2010-0081354 | A | 7/2010 |
| KR | 10-2011-0065338 | A | 6/2011 |
| WO | 9608892 | A1 | 3/1996 |
| WO | 2008050402 | A1 | 5/2008 |
| WO | 2012/127971 | A1 | 9/2012 |
| WO | 2013/182733 | A1 | 12/2013 |
| WO | 2019064453 | A1 | 4/2019 |
| WO | 2020/042755 | A1 | 3/2020 |
| WO | 2023/009477 | A1 | 2/2023 |

OTHER PUBLICATIONS

Texas Advanced Optoelectronic Solutions Inc., TCS230 Programmable Color Light-To-Frequency Converter, Dec. 2007, 12 pages.
Methven, Don, Wireless Video Streaming: An Overview, Nov. 16, 2022, 7 pages.
Outdoorlink, Inc., SmartLink One, One Relay, http://smartlinkcontrol.com/billboard/one-relay/, retrieved Apr. 17, 2019, 2007-16, 6 pages.
Outdoorlink, Inc., SmartLink Website User Manual, http://smartlink.outdoorlinkinc.com/docs/SmartLinkWebsiteUserManual.pdf, 2017, 33 pages.
Outdoorlink, Inc., SmartLink One Out of Home Media Controller, 2016, 1 page.
Sigmasense, Analog can't touch Digital, https://sigmasense.com/, retrieved Jan. 23, 2019, 5 pages.
Sigmasense, Solutions, https://sigmasense.com/solutions/, retrieved Jan. 23, 2019, 4 pages.
Sigmasense, Technology, https://sigmasense.com/technology/, retrieved Jan. 23, 2019, 3 pages.
Turley, Jim, SigmaSense ICCI Goes Big, New Touch Technology Aimed at Big Screens, But That's Just for Starters, EEJournal, https://www.eejournal.com/article/sigmasense-icci-goes-big/, Jan. 8, 2019, 3 pages.

\* cited by examiner

SYSTEMS AND METHODS FOR AUTOMATED, ARTIFICIAL INTELLIGENCE BASED MONITORING OF, AND/OR ALERTING FOR, DIGITAL OUT OF HOME DISPLAY UNITS

CROSS-REFERENCE TO RELATED APPLICATIONS

This application is filed as original and makes no priority claim.

TECHNICAL FIELD

Exemplary embodiments relate generally to systems and methods for automated, artificial intelligence (AI) based monitoring of, and/or alerting for, digital out of home (DOOH) display units.

BACKGROUND AND SUMMARY OF THE INVENTION

DOOH display units (sometimes also referred to herein as "units") are becoming increasingly popular, especially in relatively urban and/or high traffic environments. Such units are often used for advertising purposes, but may also or alternatively, be used to make public announcements, provide wayfinding, emergency services, wireless communication, or other features. At a high level, local and remote based monitoring and controlling such units is known, including various alerting features and such as based on various on-board sensor data.

To facilitate large scale manufacture and operation, broad-based control schemes are generally utilized for such monitoring and control. For example, cooling fans and backlight illumination may be operated based on local and/or remote sensor data in accordance with a series of operating rules and parameters. As temperature sensors report increasing temperature, cooling fans may be ramped up and/or backlight levels may be decreased, for example.

Ambient conditions, including air temperature and solar loading, are sometimes used to control certain display operations. For example, ambient air temperature may be used to control fan speed (for cooling), ambient light levels may be used to control display brightness (for visual quality) and/or fan speed (for cooling), and time of day may be used to control display brightness (for visual quality) and/or fan speed (for cooling). Such control may be exerted based on local and/or remote sensor data (e.g., internet reported local weather conditions, local sunrise/sunset, local temperature sensor, local ambient light sensor).

However, challenges arise with control of these units as they experience a wide variety of conditions, such as depending on installation geography/climate, individual surroundings (e.g., shade/sun, unit face direction), seasonal condition variations, daily condition variations, and so on. Solar loading, for example, is one of the largest, sometimes the largest, source of thermal load in such units, particularly on electronic display faces or covers therefor and/or large area covers/doors/access panels/cladding/housing. The impact of solar load, however, varies greatly based on individual unit installations—e.g., geography/climate, shade levels, display face size, display face direction, and so on. To provide context, such units may include 55", 75", or even 92"+ size displays, with cover layers being even larger. Such a large surface, exposed to full sunlight, particularly in relatively solar intense geographies such as Florida, Texas, Abu Dhabi, and so on, can result in significant solar loading.

By way of example, two units could be installed roughly next to each other on a sidewalk, but if one is shaded and the other is not, that can significantly impact conditions experienced given that solar loading. Furthermore, the urban landscape where such units are normally installed is a rapidly changing one. Thus, even where a unit has historically been shaded or exposed to sun, a new building could be erected or a structure removed which suddenly exposes it to sunlight, or vise-versa. In this regard, internet reported local conditions are not always helpful for the individual unit. Furthermore, even locally sensed/reported conditions can be unreliable. For example, an ambient light sensor might be shaded at times by a sign, car, pedestrian, user, or so on, while the remaining display face receives sunlight. This can lead to less than ideal operations, particularly when applying control schemes to an individual display or network of display units.

As another example, internet sourced weather conditions could vary significantly from the conditions experienced at an individual unit. For example, near a city sidewalk and road, temperatures tend to run higher. Above the sidewalk and road, temperatures may be lower. Even at a specific unit, local sensor placement might affect measured conditions.

Additionally, there is a complex relationship between ambient conditions and display unit operations, individual display monitoring, alerting, and diagnosis typically requires manual, subjective review, analysis, testing, and inspection for verification. To provide a more specific example of these complex relationships, ingesting relatively cool air into a relatively warm unit can cause rapid condensation of air moisture, resulting in internal condensation formation, which is undesirable given the sensitive electronics within such units and/or need for visual clarity. Notably, while these units sometimes have "closed" areas which are partitioned from an ambient environment, such as in accordance with ingress protection (IP) code IP55, 56, 57, 65, 66, and/or 67 available from the international electrotechnical commission (https://www.iec.ch/ip-ratings, accessed Aug. 22, 2025 at 3:40 PM ET, incorporated by reference) to provide ruggedization and/or protection of such sensitive electronics, such closed areas are not typically hermetically sealed. As another, related example, while not hermetically sealed, these closed areas may be sufficiently sealed that temperature changes affect internal pressures, which can affect component integrity. Thus, there is a strong interest in accurately monitoring operation and exerting operational control over such units, but a technical challenge in doing so accurately from afar, even with local sensor data.

Furthermore, the nature of gasses used to cool such units (ambient air ingested through open airflow pathways, or circulating gas utilized in closed areas) makes even relatively small manufacturing variations sometime result in relatively pronounced variation in operating conditions. For example, incomplete fusion from welds, incomplete sealing from fasteners, incomplete application of adhesive or sealant materials, incomplete adhesion, misplaced or missing sealing elements (e.g., O-rings, gaskets), poor or compromised parts (e.g., having impurities), combinations thereof, and the like, can all attribute to individual unit performance variations, which can be particularly pronounced with gasses, which can expand or contract to move through even very small voids. For example, leaking between "open" (e.g., intentionally exposed to ambient environment, such as via intakes and/or exhausts, even if filtered) and closed areas, or conversely unexpected well sealed units, can result in unexpected air composition, pressure changes, and so forth. To complicate matters further, even relatively small pressure changes over the relatively large surfaces of such units (e.g., 55", 75", 92", etc. size displays and other surfaces) can result in relatively high levels of forces experienced at such surfaces. Even with local based sensor data, remotely diagnosing complications from these, and other issues, is technically challenging as they can present in unexpected ways.

To give yet other examples of potential complications, some units may be installed to moving vehicles, like vehicle top displays, and thereby be exposed to rapidly and unexpectedly changing conditions. Units may be installed at places, such as train stations, periodically exposed to rapidly changing conditions, such as when a train passes and creates a pressure wave, dust, and so forth.

For at least these reasons, the known, broad-based control schemes are often not as useful to individual units and situations. Furthermore, analyzing sensor data for individual units, even in an automated fashion, is not practical given the complex, often unexpected, and multi-factor relationship between all these variables, and others. No single computer algorithm can be provided to predict the world's economy or weather, for example.

To solve these, and other field-specific technical challenges, systems and methods are disclosed which provide automated, AI based monitoring of, and/or alerting for, DOOH units. Historical data for units may be tagged, stored, and used to train an artificial intelligence (AI) model, preferably a neural network based model. The historical data may be tagged as one: normal and abnormal, and the latter preferably being tagged with a specific failure condition (e.g., fan failure, backlight failure, pressure leak, clogged intakes/exhaust, external actor (e.g., vandalism, car crash, combinations thereof, or the like)), in exemplary embodiments. This historical data is tagged with a unit identifier in exemplary embodiments. The historical data may include and/or be tagged with, geographic data, ambient condition data (e.g., temperature, sunrise/sunset time, weather conditions, ambient light levels, combinations thereof, or the like), date/time information, installation information, manufacture date, make/model information, history notes, repair history, service history, maintenance history, combinations thereof, or the like. Particularly where the historical data includes and/or is tagged with a leak as part of the failure condition, the historical data may include and/or be tagged with a leak type and/or location.

As new data (e.g., from sensor and/or controllers of the units) is received, it may be stored along with an applicable unit identifier. The new data may be analyzed by the AI model. Where abnormal conditions and/or the need for maintenance (such as on a preemptive/proactive basis) are found by the AI model, an alert may be generated. In exemplary embodiments, the system automatically generates a service request for the unit based on the abnormal conditions. For example, the system may assign a technician or team based on the geography of the unit, the abnormal conditions and/or the need for maintenance identified, and may include such information in the request. In this way, the relevant technician or team may be dispatched, such as with replacement parts, appropriate manuals or other information, may preemptively coordinate permitting and other actions, combinations thereof, and the like.

The findings of the dispatched technician or team may be electronically transmitted back to the AI model for improvement over time. For example, the new data corresponding to the abnormal condition may be tagged as normal or abnormal and/or with a specific failure condition based on the inspection/maintenance report of the dispatched technician or team. Particularly where the specific failure condition includes a leak, the specific failure condition may include and/or be tagged with a leak type and/or location. Such information may be communicated by way of remote electronic devices associated with the technicians or teams.

In other exemplary embodiments, acceptable operating parameters for a unit, or unit population, may be established. As new data is received, it may be reviewed against the parameters for violations (herein also referred to as abnormal conditions). Where an abnormal condition is sensed, historical data from similarly situated units (e.g., based on locations, ambient conditions, sensor data, controller data, combinations thereof, and the like) is retrieved and used to train the AI model. The abnormal data is then analyzed against the trained AI model to confirm the presence of an abnormal condition. If an abnormal condition is confirmed, a technician or team may be dispatched accordingly, such as discussed herein. In this embodiment, the AI model may be initially trained by the historical data from similarly situated units only. This may allow use of a more generalized, available AI model (e.g., as additional layer thereof) and provide more targeted historical training data for more accurate results. In other exemplary embodiments, the already trained AI model is further trained by the data from similarly situated units only. This may provide more accurate results.

Where no abnormal conditions are found, confirmed, and/or reported on inspection, the new data may be tagged accordingly and used as part of further analysis.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical, similar, or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
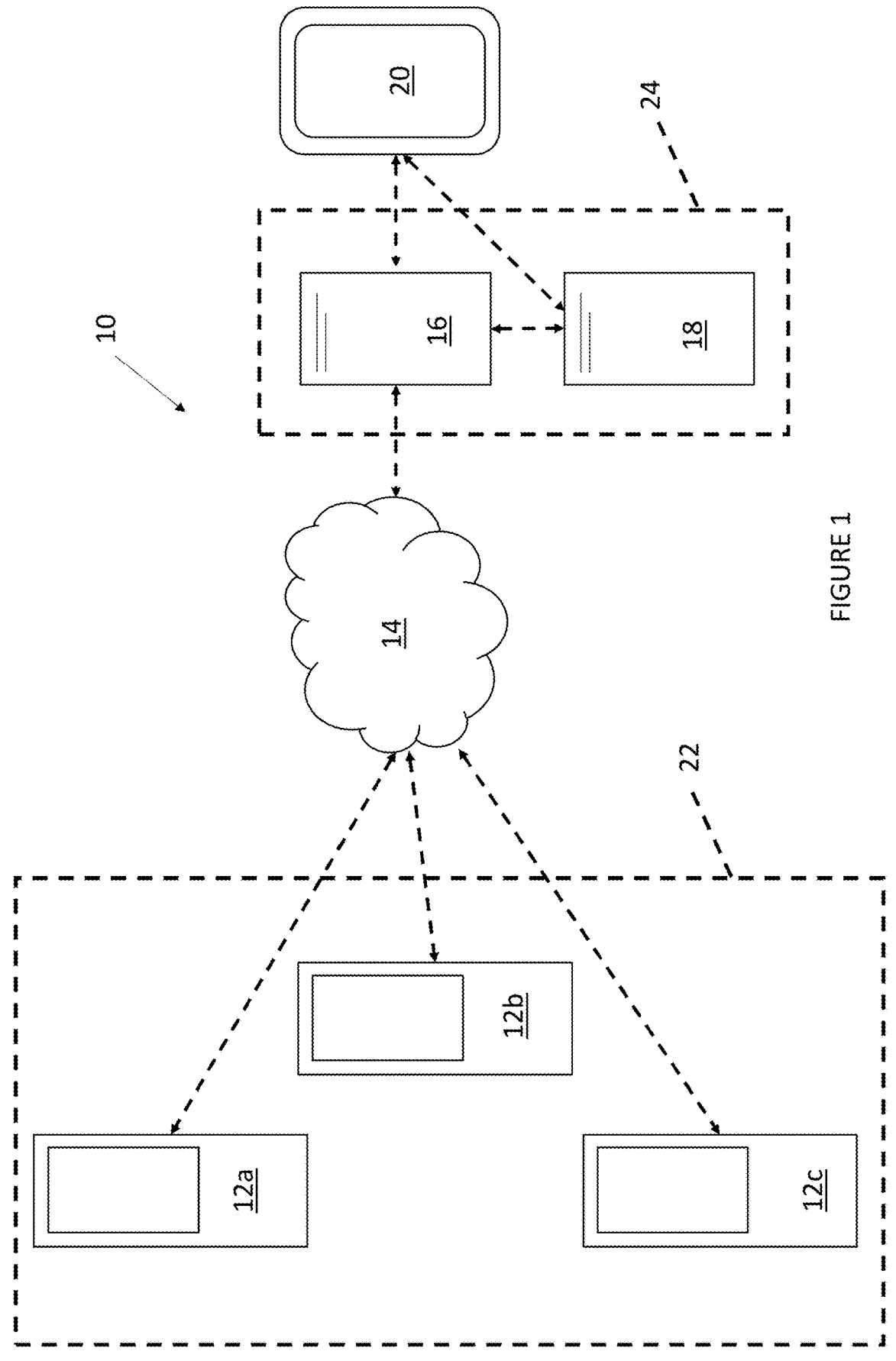
FIG. 1 is a schematic of an exemplary system for automated, AI based monitoring of, and/or alerting for, a network of DOOH display units.

FIG. 1 illustrates an exemplary system 10 for providing automated, AI based monitoring of, and/or alerting for, DOOH display units 12. A network 22 of units 12a, 12b, 12c may be provided. The network 22 may include any number and type of units 12. The network 22 may refer to units 12 which are connected to a common monitoring subsystem 24. The monitoring subsystem 24 may include one or more electronic databases 16 (e.g., server hosted), and one or more computing devices 18 (e.g., servers). The database(s) 16 and computing device(s) 18 may be provided at one or more common or separate hardware devices, such as but not limited to, servers (e.g., providing cloud based storage and computing or otherwise). The monitoring subsystem 24 may be hosted in a brick and mortar location, cloud hosted, combinations thereof, or the like.

The monitoring subsystem 24 may be in electronic communication with one or more remote electronic devices 20. These electronic devices 20 may be associated with unit 12 owners, operators, technicians, service teams, combinations thereof, or the like. The remote electronic device(s) 20 may include personal computers, laptops, tablets, smartphones, smart watches, combinations thereof, or the like. The remote electronic device(s) 20 may include an application ("app") installed or installable thereon configured to communicate with the monitoring subsystem 24.

Communications between the monitoring subsystem 24 and the remote electronic device(s) 20 may be made by way of the network(s) 14.

The number and type of units 12 and electronic device(s) 20 is exemplary, various number and/or type of such units 12 and electronic device(s) 20 may be utilized.

Figure 2:
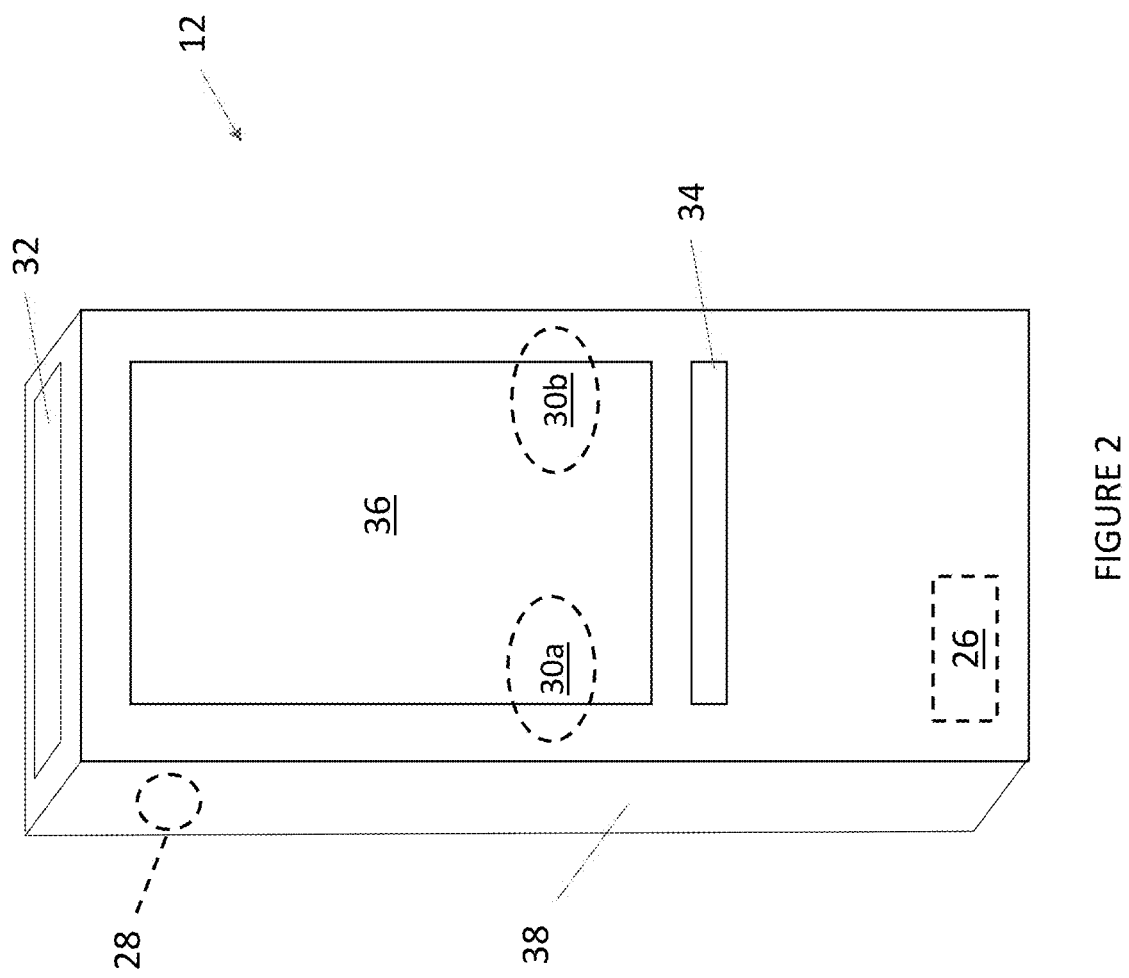
FIG. 2 is a schematic of an exemplary unit of the system of FIG. 1.

FIG. 2 illustrates an exemplary unit 12. The unit 12 includes a structural subassembly 38, which may include one or more structural members, cladding, housings, combinations thereof, or the like. The structural subassembly 38 supports a display subassembly 36. The display subassembly 36 may include a cover, an electronic display layer, an illumination layer, combinations thereof, or the like. The display subassembly 36 may include a liquid crystal display (backlit or otherwise, e.g., as an "e-ink" display), an organic light emitting diode display, a direct light emitting diode display, combinations thereof, or the like. The display assembly 36 may be movable relative to the structural subassembly 38.

An intake 32 may be provided at an upper portion of the structural subassembly 38, such as above the display assembly 36. An exhaust 34 may be located at a lower portion of structural subassembly 38, such as below the display assembly 36. Various number and arrangement of such intakes 32 and exhausts 34 may be utilized.

The unit 12 may include one or more sensors 28. Sensors 28 may include, for example without limitation, pressure sensors, temperature sensors, humidity sensors, light sensors, airflow sensors, power sensors, shock sensors, vibration sensors, tilt sensors, location sensors, combinations thereof, or the like.

The unit 12 may include one or more fans 30, such as for thermal management of the unit 12. Some of the fan(s) 30 may be provided within "closed" areas of the unit 12. These fan(s) 30 may be sometimes referred to herein as closed fans 30a. The closed areas may be areas of the units 12 which are partitioned from an ambient environment, ambient air, and/or "open" areas in accordance with IP code IP55, 56, 57, 65, 66, and/or 67. The closed areas may be part of airflow pathway(s) which extend within the unit 12, such as within the display subassembly 36. Some of the fan(s) 30 may be provided within "open" areas of the unit 12. These fan(s) 30 may be sometimes referred to herein as open fans 30b. The open areas may be part of airflow pathway(s) which extend within the unit 12, such as within the display subassembly 36, and may be accessible to the ambient environment, such as by way of the intake(s) 32 and/or exhaust(s) 34. The open areas and/or closed areas may be provided with, or without, some or all of the fans 30.

The units 12 may comprise one or more electronics 26, such as but not necessarily limited to, controllers, processors, non-transitory electronic storage devices, servers, cameras, network communication equipment, power supplies, combinations thereof, or the like. As used herein, "controllers" may include one or more computing devices, logic boards, processors, non-transitory electronic storage devices, combinations thereof, or the like.

Each unit 12 may include a single or multiple display subassemblies 36.

The units 12 may be, in whole or in part, as shown and/or described in US Pub No. 2024/0032238 published Jan. 25, 2024, US Pub. No. 2025/0227902 published Jul. 10, 2025, US Pub. No. 2023/0164964 published May 25, 2023, US Pub. No. 2023/0056061 published Feb. 23, 2023, US Pub. No. 2023/0160774 published May 25, 2023, US Pub. No. 2023/0333423 published Oct. 19, 2023, and/or US Pub. No. 2022/0132681 published Apr. 28, 2022, US Pub. No. 2019/0339312 published Nov. 7, 2019, US Pub. No. 2024/0144806 published May 2, 2024, US Pub. No. 2023/0048815 published Feb. 16, 2023, and/or may contain some or all components thereof, and/or operate in whole or in part as provided therein, the disclosures of each of the foregoing being hereby incorporated by reference as if fully restated herein.

Figure 3:
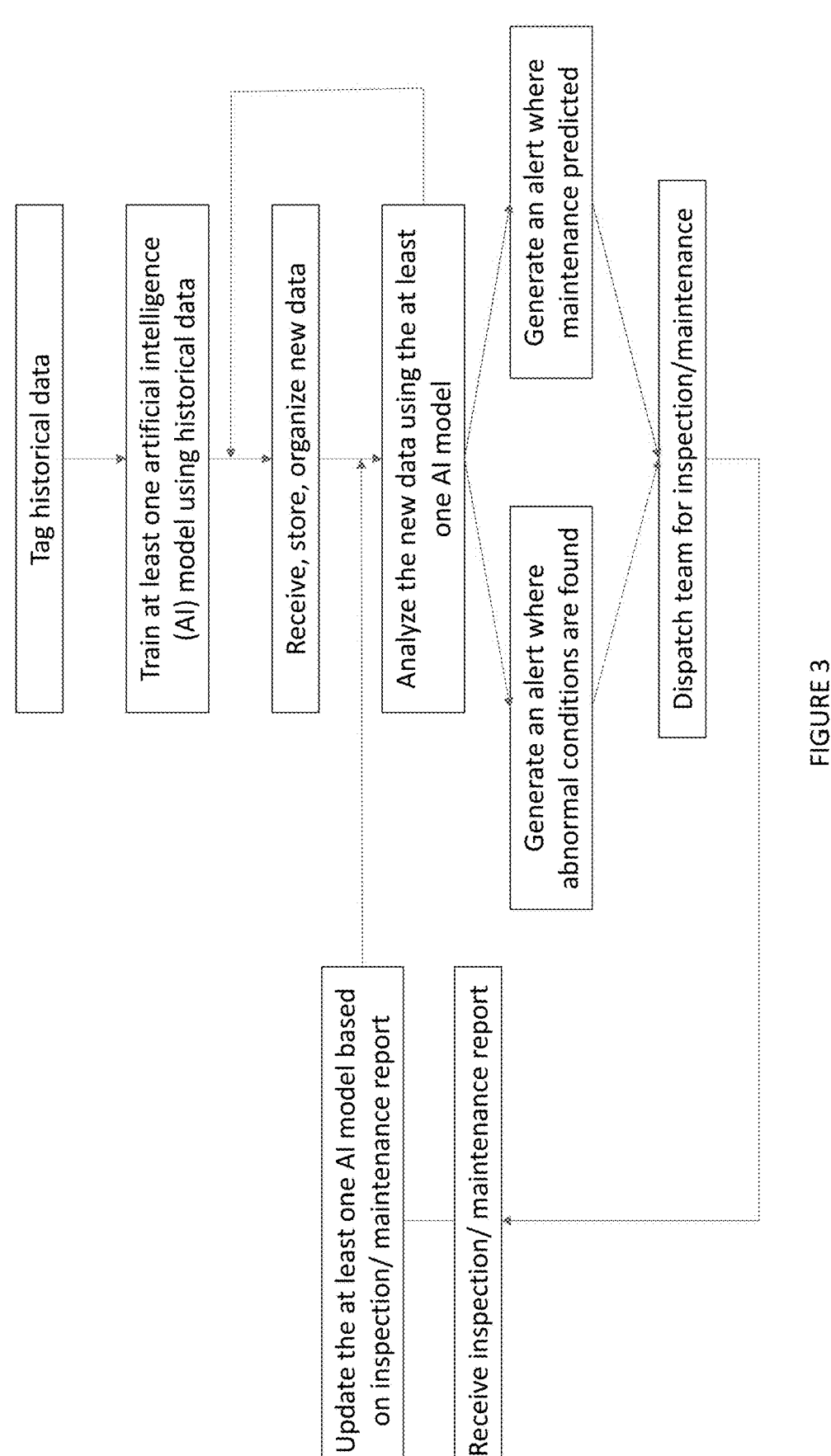
FIG. 3 is a flow chart with exemplary logic for operating the system of FIG. 1.

FIG. 3 illustrates exemplary logic for operating the system 10 and/or units 12. Historical data may be obtained, such as by data reported from the units 12 to the monitoring subsystem 24 and/or stored at the database(s) 16 thereof. The data may include data from some or all of the sensor(s) 28 (sometimes referred to herein as sensor data), data from some or all of the electronic(s) 26, such as regarding unit 12 operations (e.g., fan speed and/or status, backlight levels and/or status, display assembly 36 and/or related components (e.g., video player, touch screen components, peripheral equipment) operations and/or status (e.g., images displayed, on/off status, operational status), power consumption levels, combinations thereof, and the like), local condition information (e.g., ambient weather, sunrise/sunset conditions, ambient noise, camera images, combinations thereof, and the like; optionally derived from internet based sources), combinations thereof, and the like. The data from the electronic(s) 26 and/or local conditions are sometimes referred to herein as operational status data. The data may include any or all of the data shown and/or described in the above referenced published applications that are incorporated by reference. This data may include artificially generated data, such as designed to simulate certain conditions.

The data from a given sensor 28 or electronic 26 may describe one or more particular characteristics of the display unit 12, a component thereof, operating conditions within and/or about the unit 12, or a component thereof. The data may describe the condition(s) directly, or condition(s) may be derived from the data (e.g., the data itself may not be human-interpretable, and/or further computational analysis may be required to drive the characteristic reading in question). For example, without limitation, a temperature sensor 28 reading may be provided, or data from the sensor 28 may be provided which may be computer-interpretable as, or into, a temperature reading. As another example, data from a fan 30 may indicate fan speed, or data from a controller 26 may indicate commanded fan speed. As yet another example, temperature and/or humidity data may be obtained from local sensors 28 and/or internet based reporting and used to derive a dew point spread (DPS) for the unit 12. These are just some, of many, examples.

The historical data may be tagged, such as on a manual or automated basis. Such tagging may include a unit identifier, which may be a unique, alphanumeric code in exemplary embodiments. In exemplary embodiments, all data originating from a particular unit 12 is automatically tagged with a respective unique identifier. Preferably, such tagging includes a normal or abnormal identifier. And, in exemplary embodiments, where such tagging includes an abnormal identifier, the data is further tagged with a specific respective failure condition (e.g., of a plurality of candidate failure conditions). Particularly where the historical data includes and/or is tagged with a leak as part of the failure condition, the historical data may include and/or be tagged with a leak type and/or location. For example, without limitation, the leak location may include indications such as open loop, closed loop, high pressure side (of open or closed loop fan), low pressure side (of open or closed loop fan), combinations thereof, or the like.

At least one AI model is trained with this historical, tagged data. The AI model(s) preferably include at least one neural network model. Other types of AI models may be utilized in other embodiments. The AI model(s) may be stored at and/or executed by the computing device(s) 18.

As new data is received, such as at the monitoring subsystem 24, it may be stored (e.g., at the database(s) 16) and organized, such as with at least a unit identifier tag. The new data may be analyzed by the AI model(s). Where the AI model(s) perceive an abnormal condition and/or a predicted need for maintenance within a predetermined time window (e.g., 1 month), the computing device(s) 18 may generate an alert accordingly. The computing device(s) 18 may be configured to transmit the alert to one or more of the electronic device(s) 20. In exemplary embodiments, the alerts are transmitted to certain of the device(s) 20 affiliated with the display identifier (e.g., as stored at the database(s) 16, such as unit 12 operators and/or owners).

In exemplary embodiments, the alerts are transmitted to certain of the device(s) 20 affiliated with a technician or team for servicing the unit 12 in question. For example, each of the technician or team may be associated with a geographic service area, and the alert may be transmitted to the technician or team having an associated geographic service area encompassing the unit's 12 location. As another example, without limitation, each of the technician or team may be associated with a skill set, and the alert may be transmitted to the technician or team having a skill set associated with the perceived abnormal condition or predicted maintenance. These determinations may be made by way of database lookup, for example.

The alert may include the perceived abnormal condition or predicted maintenance, which may allow the assigned technician or team to come to the service event prepared, such as with applicable parts, tools, manuals, permits, combinations thereof, and the like. This may also allow for pre-analysis of the data, engineering/manufacturing consults, remote diagnostics, and so forth to improve the service event. The alert may include links and/or prompts for the same.

The system 10 may be configured to automatically generate calendar schedules for the service event and/or account for electronically identified technician or team availability, such as using an electronic calendar.

Inspection/maintenance reports may be received from the devices 20, such as at the monitoring system 24. The inspection/maintenance reports may include findings based on the service event associated with the alert. The relevant data triggering the alert may be tagged with the findings of the inspection/maintenance reports, such as abnormal, normal, service performed, maintenance performed, service not needed, maintenance not needed, and/or a specific failure condition. In this way, the AI model(s) may be improved over time.

The inspection/maintenance reports may be analyzed by the computing device(s) 18, such as using one or more large language models (which may be part of or separate from the AI model(s)) to derive the findings. This may allow use of natural language by technicians and teams and may provide more nuanced understanding of failure conditions, maintenance needs, and underlying causes. Alternatively, or additionally, the inspection/maintenance reports may include one or more standardized codes or failure conditions or maintenance needs (e.g., selected from candidate lists). This may allow for more efficient comparison against other data. In exemplary embodiments, a combination of the foregoing is used, such as standardized codes or failure conditions or maintenance needs and use of natural language/LLM analysis where an "other" type of option is selected (e.g., where the standardized options do not provide for the specific situation or are otherwise insufficient).

The approach provided herein may allow for the AI model to be trained and improved based on real world conditions, which may allow for more accurate alerting, and optionally automated and improved servicing requests. For example, the approach provided herein may allow for abnormal conditions and/or predictive maintenance to be identified across previously unidentified associations, compensate for ambient conditions, compensate for geography, combinations thereof, and the like.

Figure 4:
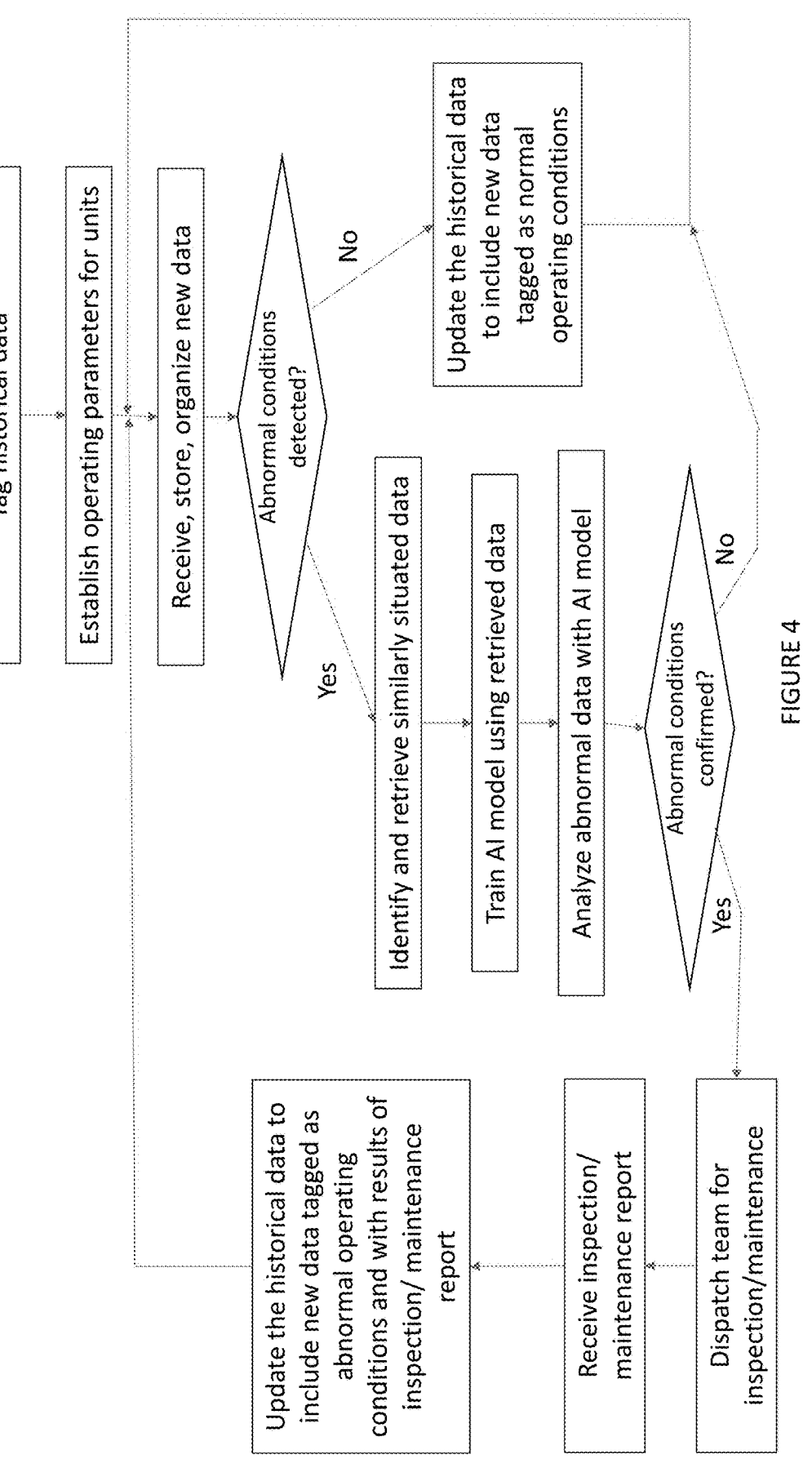
FIG. 4 is a flow chart with other exemplary logic for operating the system of FIG. 1.

FIG. 4 provides another exemplary approach. The historical data may be similarly tagged. Operating parameters for the units 12 may be established. These may include upper limits, lower limits, relative limits, ranges (acceptable and unacceptable), relative limits, rates, combinations thereof, and so forth. This may allow broad rules to be established for all units 12, such as in a simplified fashion that is less computationally expensive, preserves safety limits, and the like.

As new data is received for the units 12, it may be analyzed against these parameters, such as by the computing device(s) 18. Where it is outside of one or more of the parameters, similar historical data may be retrieved from the database(s) 16. Such similar data may include one or more of: data from the same unit 12, data from geographically proximate units 12, data from units 12 having similar ambient conditions, data from units 12 having similar operating conditions, data from units 12 having similar sensor 28 data, data from units 12 having similar parameter violations, combinations thereof, or the like. Similar, proximate, and the like may be within predetermined ranges (e.g., +/–X %, +/–X value, combinations thereof, or the like). Similarity may be, at least as to certain of the data, parameter specific, in exemplary embodiments. For example, where a closed area temperature parameter is violated, data from units 12 having similar sensor 28 data from a same or similarly placed temperature sensor may be utilized. However, even in such embodiments, other (or preferably all) data from the similar unit 12 is retrieved for training. This may permit connections to be established that may otherwise be left undiscovered. This may allow for a smaller universe of data to be considered by the AI model(s) for training, thereby leading to more accurate results, faster processing (e.g., of training and/or subsequent analysis), more efficient use of computing resources, and so forth. These considerations may be particularly important to provide relatively rapid, customized analysis required, as model training can otherwise consume significant time and resources.

An existing AI model(s), such as developed under some or all of the approach shown and/or described by FIG. 3, or a general purpose AI model (e.g., neural network based LLM), may be trained with the retrieved, similar data. This may produce newly trained AI model, a modified AI model, and/or an additional AI layer on top of the existing AI model, and may be referred to herein as the modified AI. The abnormal data may then be analyzed with the modified AI to confirm/deny that the abnormal condition exists. If the abnormal condition does exist, alerts and servicing dispatch, along with relevant results reporting and model improvement may be performed, such as in the same or substantially the same way as shown and/or described with regard to FIG. 3.

Where an abnormal condition is not detected or not confirmed, the new data may be tagged as such and stored. In other exemplary embodiments, such data is discarded.

This approach may be more computationally efficient, such as by triggering the AI model usage only where an abnormal condition is first sensed. This approach, alternatively or additionally, may provide more accurate results, such as by using a narrower universe of similar data to modify the AI, making it more accurate of the specific condition. This may also permit leverage of a more generalized AI model. This may also permit for faster training and analysis, because a smaller universe of data is being considered.

In exemplary embodiments, without limitation, certain condition monitoring, failure condition identification, and/or service request dispatch may include some or all of teachings of US Pub. No. 2021/0397292 published Dec. 23, 2021, which is hereby incorporated by reference as if fully restated herein.

In exemplary embodiments, without limitation, the AI model(s), upon training and/or further training, may be configured to evaluate incoming data for downward trends in dew point spread (DPS), which may be indicative of a leaky unit. Alternatively, or additionally, the AI model(s) may be configured to evaluate incoming data for downward trends in peak to peak pressure cycles, which typically occur on an at least daily basis and/or with certain events. These techniques may be as shown and/or in described in one or more of the aforementioned, incorporated by reference, published applications and/or U.S. Pat. No. 10,782,276 issued Sep. 22, 2020, which is hereby incorporated by reference as if fully restated herein, by way of example.

Figure 5:
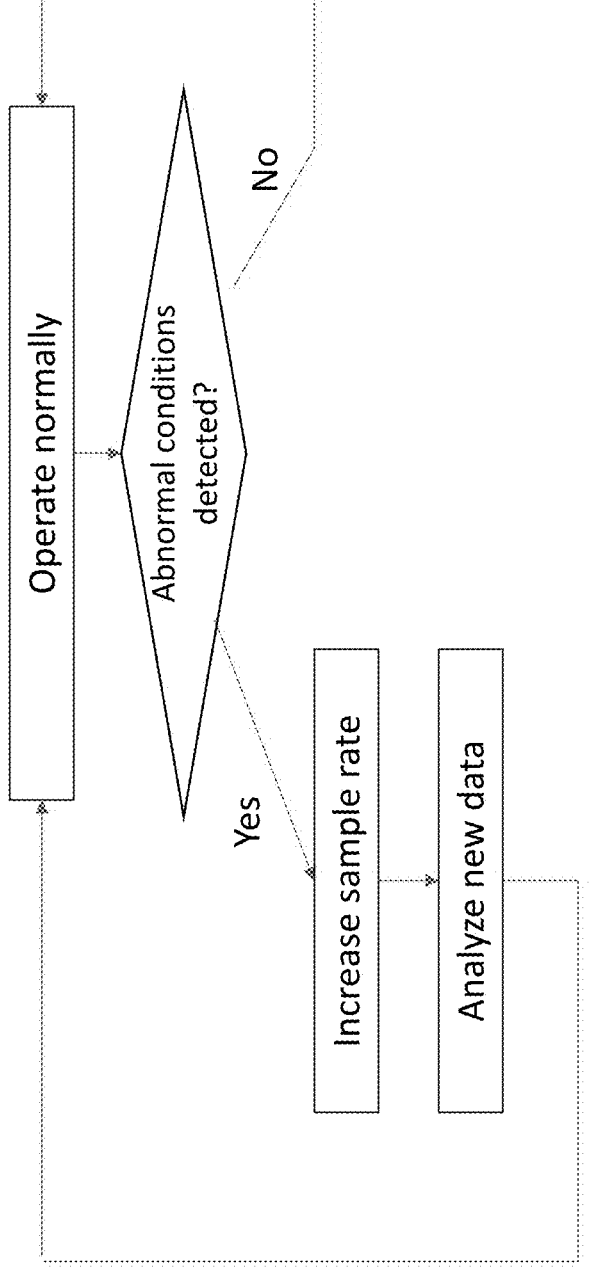
FIG. 5 is a flow chart with other exemplary logic for operating the system of FIG. 1 and/or as part of the methods of FIGS. 2-4.

FIG. 5 provides exemplary logic for the system and/or methods provided herein. Normally, the units 12 may be configured, such as by way of the electronics 26, sensors 28, and/or other components, to take and/or report data samples at a first time interval (e.g., every 1 minute, 30 seconds, 10 seconds, etc.). Where an abnormal condition is detected, the units 12 may be configured to increase the sample rate to a second time interval which is shorter than the first time interval (e.g., every second, $\frac{1}{10}^{th}$ second, 5 seconds, etc.) This may increase the availability of data during periods of abnormality to better understand unit 12 conditions while also preserving electronic storage space (e.g., database 16) and/or computational resources, leading to increased efficiency. The sample rate increase may be for a predetermined period of time (e.g., 5 minutes, 2 minutes, 30 minutes, etc.), until normal conditions are detected, or the like.

Figure 6:
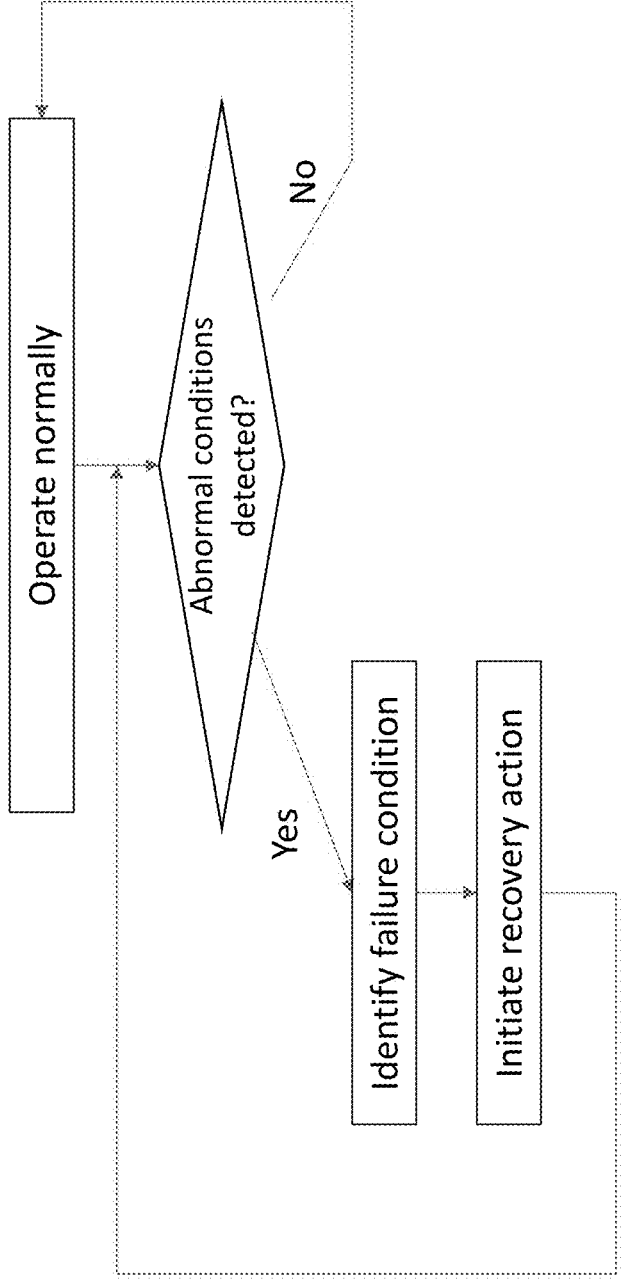
FIG. 6 is a flow chart with other exemplary logic for operating the system of FIG. 1 and/or as part of the methods of FIGS. 2-5.

FIG. 6 provides exemplary logic for the system and/or methods provided herein. The units 12 may be configured, such as by way of the electronics 26, to operate under default operational scheme(s). These may include, by way of example and without limitation, adjusting display subassembly 36 illumination levels based on ambient light conditions, adjusting fan 30 speeds based on sensor 28 data (e.g., temperature, mitigate condensation formation, etc.), and the like. However, where abnormal conditions are detected, such as through one or more of the approaches shown and/or described herein, an attempt may be made to identify a failure condition. In exemplary embodiments, the computing device(s) 18 execute the at least one AI model to identify a predicted failure condition based on stored data at the database(s) 16 from similarly situated units 12 and known associated failure conditions. These may include, by way of example and without limitation, overheating, overcooling, condensation formation, leaking, and the like. Based on the failure condition identified, the monitoring subsystem 24 may be configured to initiate a recovery action. A plurality of candidate recovery actions may each be associated with one or more of the failure conditions, such as in a predetermined fashion and retrieved via database lookup. In other exemplary embodiments, the AI model(s) may be permitted to select recovery actions from the candidate recovery actions, such as based on historical data indicating recovery actions that were successful and unsuccessful.

Particularly where the historical data includes and/or is tagged with a leak as part of the failure condition, the historical data may include and/or be tagged with a leak type and/or location. For example, without limitation, the leak location may include indications such as open loop, closed loop, high pressure side (of open or closed loop fan), low pressure side (of open or closed loop fan), combinations thereof, or the like. In exemplary embodiments, this may be determined by sensor location, specific testing conditions, combinations thereof, or the like.

Examples of recovery actions include, but are not limited to, overheating may be associated with increased fan 30 speeds and/or decreased display subassembly 36 illumination levels (including but not limited to, down to zero, such as part of a temporary shutdown), overcooling may be associated with decreased fan 30 speeds and/or increased display subassembly 36 illumination levels, condensation formation may be associated with decreased open fan 30*b* speeds, increased or maintained closed fan 30*a* speeds, and/or increased display subassembly 36 illumination levels, and leaking may be associated with increased fan 30 speeds. These remedial actions may be implemented by electronic command from the monitoring subsystem 24 to the display unit 12 in question. In exemplary embodiments, the closed fans 30a are kept running at some level, preferably at a level between 50-100%, while the open fans 30b are adjusted, such as between 0-100%. Where a failure condition cannot be identified, a default recovery sequence may be initiated, such as a temporary shut down and reboot. The remedial actions may include some or all of the teachings of US Pub. No. 2024/0144806 published May 2, 2024, which is incorporated by reference as if fully restated herein.

While discussion is sometimes made herein of analysis or other actions at the monitoring subsystem 24, in other exemplary embodiments, the analysis or other actions may be implemented locally, such as at the display units 12.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention.

Certain operations described herein may be performed by one or more electronic devices. Each electronic device may comprise one or more processors, electronic storage devices, executable software instructions, combinations thereof, and the like configured to perform the operations described herein. The features and/or functionality shown and/or described herein may be accomplished by way of stored, executable software instructions, such as in the form of applications, programs, routines, combinations thereof, or the like. The electronic devices may be general purpose computers or specialized computing devices. The electronic devices may comprise personal computers, smartphones, tablets, databases, servers, or the like. The electronic connections and transmissions described herein may be accomplished by one or more wired or wireless connectivity components (e.g., routers, modems, ethernet cables, fiber optic cable, telephone cables, signal repeaters, and the like) and/or networks (e.g., internets, intranets, cellular networks, the world wide web, local area networks, and the like). The computerized hardware, software, components, systems, steps, methods, and/or processes described herein may serve to improve the speed of the computerized hardware, software, systems, steps, methods, and/or processes described herein. The electronic devices, including but not necessarily limited to the electronic storage devices, databases, controllers, or the like, may comprise and/or be configured to hold, solely non-transitory signals.

What is claimed is:

1. A system for automated, artificial intelligence ("AI") based monitoring of, and alerting for, display units for digital out of home applications, said system comprising:

the display units, each installed at a respective geographic location and including a structural subassembly, a display subassembly connected to the structural subassembly, sensors for measuring conditions at the respective display unit, airflow pathways, fans for cooling the display units located along the airflow pathways, and electronics for operating the display units, including controlling the display subassembly, controlling the fans, and receiving data from the sensors; and a monitoring subsystem in electronic communication with the display units, the monitoring subsystem comprising one or more non-transitory electronic storage devices comprising software instructions, which when executed, configure one or more processors of the monitoring subsystem to:

receive data from the display units, including sensor data and operational status data;

tag the received data, including with a respective unique identifier corresponding to the respective one of the display units from which the received data originated;

analyze the received, tagged data using an AI model trained using historical data from same or different ones of the display units to identify if the received, tagged data indicates that any of the display units are experiencing any of: abnormal conditions and maintenance needs within a predetermined time period, wherein the historical data includes the sensor data and the operational status data from the same or different ones of the display units tagged as one of normal and abnormal; and generate an alert and electronic service request for each of the abnormal conditions and maintenance needs identified.

2. The system of claim 1 wherein:

the one or more non-transitory electronic storage devices comprise additional software instructions, which when executed, configure the one or more processors to:

receive the historical data;

tag the received historical data, including with the respective unique identifier corresponding to the respective one of the display units from which the received data originated and one of the normal and the abnormal indicators; and train the AI model using the historical data.

3. The system of claim 1 wherein:

the one or more non-transitory electronic storage devices comprise additional software instructions, which when executed, configure the one or more processors to:

train the AI model using the historical data before receiving the data from the display units.

4. The system of claim 1 wherein:

the one or more non-transitory electronic storage devices comprise additional software instructions, which when executed, configure the one or more processors to:

establish normal operating parameters for the display units; and analyze the received data to determine if one or more of the normal operating parameters is violated, and if so:

identify a selection of a repository of display unit data, which includes the historical data and additional historical data from the same or different ones of the display units, said additional historical data including sensor data and operational status data from the same or different ones of the display units tagged as one of normal and abnormal; and retrieve the selection of the repository of display unit data for use as the historical data for training the AI model.

5. The system of claim 4 wherein:

the selection of the repository of display unit data includes the sensor data and the operational status data from the same or different ones of the display units with conditions matching or within a predetermined margin of the received, tagged data violating the one or more of the normal operating parameters.

6. The system of claim 5 wherein:

the one or more non-transitory electronic storage devices comprise additional software instructions, which when executed, configure the one or more processors to:

train the AI model using the historical data after receiving the data from the display units and identifying the selection of the repository of display unit data.

7. The system of claim 6 wherein:

the one or more non-transitory electronic storage devices comprise additional software instructions, which when executed, configure the one or more processors to:

normally sample data from the display units at a first rate;

upon determining that one or more of the normal operating parameters is violated, sample data from the display units at a second rate, which is higher than the first rate; and analyze the data from the display units sampled at the second rate using the AI model.

8. The system of claim 1 wherein:

the AI model comprises a neural network.

9. The system of claim 1 wherein:

the one or more non-transitory electronic storage devices comprise additional software instructions, which when executed, configure the one or more processors to:

tag the received data with the normal tag where no abnormal conditions are detected.

10. The system of claim 1 wherein:

the one or more non-transitory electronic storage devices comprise additional software instructions, which when executed, configure the one or more processors to:

receive service reports in response to the electronic service requests;

analyze the service reports for findings; and tag the received data associated with the electronic service requests based on the findings in the service reports, including tagging the associated, received data with the normal tag where acceptable conditions were indicated, and the abnormal tag where abnormal conditions were indicated.

11. The system of claim 10 wherein:

the one or more non-transitory electronic storage devices comprise additional software instructions, which when executed, configure the one or more processors to:

tag the received data associated with the electronic service requests based on the findings in the service reports, including tagging the associated, received data with one of a specific failure condition and maintenance need where specific failure conditions and maintenance needs were indicated, respectively.

12. The system of claim 1 wherein:

the sensors of each of the display units comprise temperature sensors and light sensors;

the operational status data includes speed data for the fans and illumination levels for the display subassemblies of the display units; and the electronics of each of the display units comprise controllers for the fans and the display subassemblies.

13. The system of claim 1 wherein:

the sensors of each of the display units comprise a humidity sensor and temperature sensors, at least one of which is in contact with ambient air, and at least two of which are in contact with other portions of the display unit; and the electronics of each of the display units comprise a controller for receiving humidity data from the humidity sensor and temperature data from the temperature sensors, identifying a lowest temperature reading from the temperature data from the at least two temperature sensors at a given time, and calculate a dewpoint spread ("DPS") between a dew point derived from the humidity data and temperature data of the at least one temperature sensor and the lowest temperature reading, and report the DPS as part of the sensor data.

14. The system of claim 1 wherein:

the display subassemblies of the display units each comprise a cover, a liquid crystal layer, and a backlight.

15. The system of claim 1 wherein:

the sensors of the display units include location sensors;

the data received from the display units includes location data from the location sensors; and the one or more non-transitory electronic storage devices comprise additional software instructions, which when executed, configure the one or more processors to:

as part of, or before, generating the electronic service requests, and for each of the service requests, respectively:

identify a respective geographic location associated with the unique display identifier associated with the received, tagged data indicating the respective abnormal conditions or maintenance need;

identify a respective technician or service team associated with the respective geographic location; and cause the electronic service request to be transmitted to a remote electronic device associated with the respective technician or service team, said electronic service request including information identifying the respective display unit and indicating the respective abnormal conditions or maintenance need.

16. The system of claim 1 wherein:

the one or more non-transitory electronic storage devices comprise additional software instructions, which when executed, configure the one or more processors to:

for each at least certain of the abnormal conditions identified, identify a respective remedial action from a plurality of candidate remedial actions and cause the respective remedial action to be implemented at the respective display unit by electronic command.

17. The system of claim 16 wherein:

the candidate remedial actions comprise altering operating speed of the fans, altering operating levels of the display subassembly, and initiating a recovery sequence.

18. The system of claim 1 wherein:

the AI model is configured to identify the abnormal condition where the analyzed data indicates any one of: downward trends in peak to peak pressure cycles and downward trends in dew point spread.

19. A method for automated, artificial intelligence ("AI") based monitoring of, and alerting for, display units for digital out of home applications, said method comprising:

receiving data from display units at a monitoring subsystem, said data including sensor data and operational status data, each of the display units being installed at a respective geographic location and including a structural subassembly, a display subassembly connected to the structural subassembly, sensors for measuring conditions at the respective display unit, airflow pathways, fans for cooling the display units located along the airflow pathways, and electronics for operating the display units, including controlling the display subassembly, controlling the fans, and receiving data from the sensors, and the monitoring subsystem being in electronic communication with the display units and comprising one or more databases and one or more computing devices;

tagging the received data, including with a respective unique display unit identifier corresponding to the respective one of the display units from which the received data originated;

analyzing the received, tagged data using an AI model trained using historical data from same or different ones of the display units to identify if the received, tagged data indicates that any of the display units are experiencing any of: abnormal conditions and maintenance needs within a predetermined time period, wherein the historical data includes the sensor data and the operational status data from the same or different ones of the display units tagged as one of normal and abnormal; and generating an alert and electronic service request for each of the abnormal conditions and maintenance needs identified.

20. A system for automated, artificial intelligence ("AI") based monitoring of, and alerting for, display units for digital out of home applications, said system comprising:

the display units, each installed at a respective geographic location and including a structural subassembly, a display subassembly connected to the structural subassembly and comprising a cover, a liquid crystal layer behind the cover, and a backlight behind the liquid crystal layer, sensors for measuring conditions at the respective display unit, airflow pathways, fans for cooling the display units located along the airflow pathways, and a controller for operating the display units, said controller configured to control at least certain operations of the display subassembly, including illumination levels of the backlight, and at least certain operations of the fans, including operating speed levels, and receive data from the sensors, including temperature readings from temperature sensors, humidity readings from a humidity sensor, location information from a location sensor, pressure readings from pressure sensors, ambient light levels from an ambient light sensor, and dew point spread ("DPS") readings derived from the humidity readings and the temperature readings from at least one of the temperature sensors; and a monitoring subsystem in electronic communication with the display units, the monitoring subsystem comprising one or more non-transitory electronic storage devices comprising software instructions, which when executed, configure one or more processors of the monitoring subsystem to:

establish a repository of historical data including sensor data from the sensors and operational status data from the controllers for the display units, each portion of said repository of said historical data being tagged as one of normal and abnormal operating conditions;

establish normal operating parameters for the display units;

receive further data from the display units, including the sensor data and the operational status data, sampled at a first rate;

analyze the received, tagged further data to determine if one or more of the normal operating parameters is violated, and if so:

begin sampling the further data from the respective display unit at a second rate, which is higher than the first rate;

identify a selection of the historical data of the repository having at least one of the sensor data and the operational status data within a predetermined margin of the sensor data and the operational status data, respectively, of the received, tagged further data determined to be violating the one or more of the normal operating parameters;

retrieve the selection of the historical data from the repository of the historical data;

utilize the selection of the historical data to train an AI model;

analyze the further data indicated as violating the normal operating parameters, including the further data sampled at the second rate, using the AI model to identify if the received data indicates that any of the display units are likely experiencing abnormal conditions, including based on the tags applied to the selection of the historical data;

generate an alert and electronic service request for each of the abnormal conditions identified;

tag the received data indicated as violating the normal operating parameters with the abnormal tag; and add the received, tagged data to the repository of the historical data;

where any of: the analysis of the received data determines that none of the normal operating parameters is violated, and the analysis of the received data using the AI model indicates that no abnormal conditions are detected:

tag the received data with the normal tag; and add the received, tagged data to the repository of the historical data.

* * * * *